(12) United States Patent
Cho et al.

(10) Patent No.: US 8,492,126 B2
(45) Date of Patent: Jul. 23, 2013

(54) ISOLATED POLYPEPTIDE FOR INCREASING ACTIVITY OF POLYSACCHARIDE HYDROLASE AND METHODS OF USE

(75) Inventors: Hwa Young Cho, Hwaseong-si (KR); Hyun Min Koo, Seoul (KR); Jae Chan Park, Yongin-si (KR); Sung Min Park, Yongin-si (KR); In Geol Choi, Seoul (KR); Kyoung Heon Kim, Seongnam-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 253 days.

(21) Appl. No.: 12/874,670

(22) Filed: Sep. 2, 2010

(65) Prior Publication Data

US 2011/0177565 A1 Jul. 21, 2011

(30) Foreign Application Priority Data

Jan. 21, 2010 (KR) ........................ 10-2010-0005576

(51) Int. Cl.
*C12N 9/42* (2006.01)
*C07K 14/32* (2006.01)
(52) U.S. Cl.
USPC .......................................... 435/105; 165/209
(58) Field of Classification Search
USPC ....................................................... 435/105
See application file for complete search history.

(56) References Cited

U.S. PATENT DOCUMENTS

| 6,326,470 | B1 | 12/2001 | Cosgrove |
| 2007/0166805 | A1 | 7/2007 | Cosgrove et al. |
| 2008/0201123 | A1 | 8/2008 | Cosgrove et al. |

FOREIGN PATENT DOCUMENTS

WO      2010030140 A2 *   3/2010

OTHER PUBLICATIONS

AXX49355 (May 2010).*
AXX49341 (May 2010).*
AXX49335 (May 2010).*
AXX49327 (May 2010).*
Kerff, F. et al., Crystal structure and activity of *Bacillus subtilis* YoaJ (EXLX1), a bacterial expansin that promotes root colonization, Proc Natl Acad Sci U S A. Nov. 4, 2008;105(44): 16876-16881. Epub Oct. 29, 2008.
Kim, E.S. et al., Functional characterization of a bacterial expansin from *Bacillus subtilis* for enhanced enzymatic hydrolysis of cellulose, Biotechnol Bioeng. Apr. 1, 2009;102(5):1342-1353.
Yennawar, N.H. et al., Crystal structure and activities of EXPB1 (Zea m 1), a β-expansin and group-1 pollen allergen from maize, Proc Natl Acad Sci U S A. Oct. 3, 2006;103(40): 14664-14671. Epub Sep. 19, 2006.

* cited by examiner

*Primary Examiner* — Tekchand Saidha
(74) *Attorney, Agent, or Firm* — Leydig, Voit & Mayer, Ltd.

(57) ABSTRACT

An isolated polypeptide is disclosed that improves the hydrolyzing capacity of a polysaccharide hydrolase such as cellulase, is capable of binding to a polysaccharide, is deficient in polysaccharide hydrolase activity, and includes a GH45 or a pollen-allergen domain. Methods of hydrolyzing polysaccharides using the isolated polypeptide are also disclosed.

22 Claims, 2 Drawing Sheets

ISOLATED POLYPEPTIDE FOR INCREASING ACTIVITY OF POLYSACCHARIDE HYDROLASE AND METHODS OF USE

CROSS-REFERENCE TO RELATED APPLICATION

This application claims priority to Korean Patent Application No. 10-2010-0005576, filed on Jan. 21, 2010, and all the benefits accruing therefrom under 35 U.S.C. §119, the content of which in its entirety is herein incorporated by reference.

BACKGROUND

1. Field

The disclosures herein relate to an isolated polypeptide, a composition thereof, and a method of increasing polysaccharide hydrolysis activity of a polysaccharide hydrolase in the presence of the isolated polypeptide.

2. Description of Related Art

With globally increasing concern about the exhaustion of resources and pollution of the environment by overuse of fossil fuels, the development of new and renewable alternative energy resources that can stably and continuously produce energy are being considered. In the ongoing development of such alternative energy resources, the technology for producing alcohol from biomass resources has been attracting considerable attention. Biofuels are a wide range of fuels which are in some way derived from biomass.

Today, "first generation biofuels" are those made from carbohydrates in sugarcanes or starch in corn using conventional technologies. "Second generation biofuels" are those made from non-food biomass, e.g., a representative cellulosic resource, lignocellulose, which is the most abundant and fully renewable biomass on the planet. At present, biofuel production from algae, sometimes called "third generation biofuels" is also being developed.

The process of producing biofuel generally includes pretreating a biomass to facilitate saccharification, saccharifying the pretreated biomass into monosaccharides, and fermenting the monosaccharides into alcohol.

Saccharification is the process of hydrolyzing polysaccharides into soluble sugars, such as monosaccharides. Generally, saccharification is carried out using a hydrolase, although chemical hydrolysis with, for example, an acid is also possible. To improve the economic feasibility and efficiency of production of biofuel from cellulosic biomass, it is necessary to reduce current production costs. In particular, about ⅔ of the cost for producing biofuel is used in pretreatment and saccharification of cellulosic biomass, and a significant portion of the cost is spent to purchase enzymes, e.g., cellulase or hemicellulase, for degrading the biomass. In order to reduce the cost for purchasing enzymes, research is being directed to improving enzyme activity or developing novel enzymes.

SUMMARY

An isolated polypeptide effective in improving the enzymatic hydrolysis of a complex polysaccharide such as cellulose and an isolated polynucleotide encoding the polypeptide are disclosed. A method of degrading a polysaccharide in the presence of the isolated polypeptide, and a method of producing biofuel by saccharifying a polysaccharide obtained from a biomass into monosaccharides, and fermenting the monosaccharides are further disclosed.

Disclosed herein is an isolated polypeptide which (a) increases activity of a polysaccharide hydrolase, (b) is capable of binding to a polysaccharide, (c) is deficient of polysaccharide hydrolase activity, and (d) includes either a glycoside hydrolase 45 (GH45) domain or a pollen-allergen (Grp2/3) domain.

In an embodiment, the polysaccharide hydrolase may be cellulase, hemicellulase, α-amylase, glucoamylase, pectinase, xylanase, cellobiase, or a combination thereof and the polysaccharide may be cellulose, hemicellulose, glucose, xylose, pectin, xylan, or a combination thereof.

In an embodiment, the GH45 or pollen-allergen domain may be isolated from an expansin protein, an expansin-like protein or a bacterial protein. In an embodiment, the GH45 or pollen-allergen domain may be a recombinant polypeptide.

In an embodiment, the expansin protein or the expansin-like protein may be α-expansin (EXPA), β-expansin (EXPB), expanin-like A (EXLA), expansin-like B (EXLB), expansin-like group X (EXLX), *Bacillus subtilis* expansin (BsEXLX1), *Hahella chejuensis* (Hc)EXLX2 or *Stigmatella aurantiaca* (Sa)EXLX.

In an embodiment, the bacterial protein may be isolated from a bacterium selected from *Leptothrix cholodnii*, Lch; *Clavibacter michiganensis*, Cmi; *Nakamurella multipartite*, Nmu; *Frankia* sp., Fsp; *Micromonospora* sp., Msp; *Streptomyces sviceus*, Ssv; *Catenulispora acidiphila*, Cac; *Plesiocystis pacifica*, Ppa; *Herpetosiphon aurantiacus*, Hau; *Chloroflexus aurantiacus*, Cau; *Acidovorax avenae*, Aav; *Roseiflexus* sp., Rsp; *Myxococcus xanthus*, Mxa; *Stigmatella aurantiaca*, Sau; *Xanthomonas campestris*, Xca; *Ralstonia solanacearum*, Rso; *Xylella fastidiosa*, Xfa; *Pectobacterium atrosepticum*, Pat; *Dickeya zeae*, Dze, and a combination thereof.

In an embodiment, the GH45 domain may have sequence homology of at least 70% with the amino acid sequence of SEQ ID NO.1, and the pollen-allergen domain may have sequence homology of at least 70% with the amino acid sequence of SEQ ID NO.2.

Also disclosed herein is a composition including the isolated polypeptide.

Disclosed herein is a method of hydrolyzing a polysaccharide. In an embodiment, the method includes adding an amount of the isolated polypeptide effective for degrading a polysaccharide to a polysaccharide material.

In an embodiment, the amount effective for hydrolyzing a polysaccharide may be about 1 to 1000 nmole per gram of the polysaccharide. In an embodiment, the polysaccharide material may be obtained from a cellulosic or lignocellulosic biomass. In an embodiment, the cellulosic or lignocellulosic biomass may be pretreated with heat, an acidic material, a basic material, or a combination thereof.

In an embodiment, the method further comprises adding a polysaccharide hydrolase, a hydrolysis catalyst, an acid, a microorganism, or a combination thereof. In some embodiments, the hydrolase may be added simultaneously with the isolated polypeptide, while in other embodiments the hydrolase may be added after the isolated polypeptide.

In an embodiment, the method may further include, after adding the isolated polypeptide, washing unbound isolated polypeptide from the polysaccharide material.

In an embodiment, the polysaccharide hydrolase may be cellulase, hemicellulase, α-amylase, glucoamylase, pectinase, xylanase, cellobiase, or a combination thereof.

In some embodiments, the polysaccharide hydrolase may be added at a concentration of about 2 to about 60 FPU (filter paper unit) per unit gram of polysaccharide.

In an embodiment, the method may further include fermenting monosaccharides obtained by degrading the polysaccharide using microorganisms.

Also disclosed herein is a method of producing a biofuel from a polysaccharide. In some embodiments, the biofuel produced is an alcohol.

In an embodiment, the method includes adding to a polysaccharide material an amount of isolated polypeptide effective for degrading the polysaccharide, incubating at least one of a polysaccharide hydrolase, a hydrolysis catalyst, an acid or a microorganism with the polysaccharide material to obtain monosaccharides, and fermenting the monosaccharides into a biofuel using a fermenting microorganism.

BRIEF DESCRIPTION OF THE DRAWINGS

The above and other aspects, advantages and features of this disclosure will become more apparent by describing in further detail exemplary embodiments thereof with reference to the accompanying drawings, in which it should be understood that various aspects of the drawings may have been exaggerated for clarity.

DETAILED DESCRIPTION

Isolated polypeptides effective in enhancing the enzymatic hydrolysis of complex polysaccharides are disclosed. The isolated polypeptides do not have polysaccharide hydrolytic activity, but are able to increase product yield from polysaccharide hydrolase reactions. The isolated polypeptides can bind to a polysaccharide, e.g. a cellulose fiber. Without being bound by theory, it is believed that binding of the isolated polypeptides to the polysaccharide enables more effective degradation of the polysaccharide by enzymatic or nonenzymatic hydrolysis. Such characteristics of the isolated polypeptide allow it to be used to enhance degradation of a polysaccharide material. In particular, when used in conjunction with a polysaccharide hydrolase, the amount of hydrolase necessary may be reduced, thereby decreasing costs associated with saccharification of biomass.

Various exemplary embodiments will now be described more fully with reference to the accompanying drawings in which exemplary embodiments are shown. This invention may however, be embodied in many different forms, and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" "connected to" another element or layer, the element or layer can be directly on or connected to another element or layer or intervening elements or layers. In contrast, when an element is referred to as being "directly on" another element, there are no intervening elements present. As used herein, the term "and/or" includes any and all combinations of one or more of the associate listed items.

It will be understood that, although the terms first, second, third etc. may be used herein to describe various elements, components, regions, layers and/or sections, these elements, components, regions, layers or sections should not be limited by these terms. These terms are only used to distinguish one element from another element, component, region, layer or section. Thus, a first element, component, region, layer or section could be termed a second element, component, region, layer or section without departing from the teachings of the present invention.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terms used herein have the following meanings unless described specifically. All technical and scientific terms used herein have meanings commonly understood by those of ordinary skill in the art.

The term "increase activity of a hydrolase" refers to an increase in the apparent activity of a given amount of a hydrolase in producing reducing sugar from a given amount of polysaccharide.

The term "isolated" refers to a change from a natural state, that is, changed and/or removed from its original environment by human means. For example, a polynucleotide or polypeptide naturally present in an organism is not "isolated," but the same polynucleotide or polypeptide when separated from a natural co-existing substance by the action of a human is "isolated." Further, a polynucleotide or polypeptide introduced into an organism in which it is not naturally present, such as a host cell, by transformation, genetic manipulation, or other recombination methods is "isolated", even if present in the organism.

The term "polypeptide" refers to any peptide including two or more amino acids joined by peptide bonds or modified peptide bonds. "Polypeptide" refers to both short chains, commonly referred to as peptides, oligopeptides or oligomers, and longer chains. Polypeptides may contain amino acids other than the 20 gene-encoded, naturally occurring amino acids. Polypeptides include amino acid sequences modified either by natural processes or by chemical modification techniques known in the art. Such modifications include acetylation, acylation, ADP-ribosylation, amidation, biotination, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see Proteins-Structure and Molecular Properties, 2nd Ed., T. E. Creighton, W. H. Freeman and Company, New York, 1993; Wold, F., Post-translational Protein Modifications; Perspectives and Prospects, pgs. 1-12 in Post-translational Covalent Modification of Proteins, B. C. Johnson, Ed., Academic Press, New York, 1983; Seifter et al., "Analysis for protein modifications and nonprotein cofactors", Meth Entzymol 182:626-646, 1990; and Rattan et al., "Protein Synthesis: Post-translational Modifications and Aging", Ann NY Acad Sci 663:48-62, 1992).

The term "polynucleotide" generally refers to any polyribonucleotide or polydeoxyribonucleotide, which may be unmodified or modified. The term "polynucleotide" includes single and double-stranded DNA, DNA that is a mixture of single and double-stranded regions, single and double-stranded RNA, RNA that is a mixture of single and double-stranded regions, and hybrid molecules including DNA and RNA that are mixtures of single and double-stranded regions. In addition, "polynucleotide" refers to triple-stranded regions including RNA, DNA, or both RNA and DNA. "Polynucleotide" includes relatively short chains, often referred to as oligonucleotides, as well as longer chains.

The term "variant" refers to a polynucleotide or polypeptide that differs from a reference polynucleotide or polypeptide, but retains its essential properties. A typical variant of a polynucleotide differs in nucleotide sequence from another variant, and from the reference polynucleotide. Changes in the nucleotide sequence of a variant may or may not alter the amino acid sequence of a polypeptide encoded by the reference polynucleotide. Nucleotide changes may result in amino acid substitutions, additions, deletions, fusions and truncations in the polypeptide encoded by the reference sequence. A typical variant of a polypeptide differs in amino acid sequence from another variant, and from the reference polypeptide. Generally, differences are limited so that the sequences of the reference polypeptide and the variant are closely similar overall and, in many regions, identical. A variant and reference polypeptide may differ in amino acid sequence by one or more substitutions, additions, and deletions in any combination. A substituted or inserted amino acid residue may or may not be one encoded by the genetic code.

Conservative amino acid substitutions may be carried out based on, for example, polarity, charge, solubility, hydrophobicity, hydrophilicity, and/or amphiphilicity of corresponding residues. For example, amino acids may be classified into nonpolar (hydrophobic) amino acids, polar but neutral amino acids, positively charged (basic) amino acids, and negatively charged (acidic) amino acids. Nonpolar (hydrophobic) amino acids include alanine, leucine, isoleucine, valine, proline, phenylalanine, tryptophan and methionine. Polar but neutral amino acids include glycine, serine, threonine, cysteine, tyrosine, asparagine and glutamine. Positively charged (basic) amino acids include arginine, lysine and histidine and negatively charged (acidic) amino acids include aspartic acid and glutamic acid. Substitution may be possible within each group. Some possible substitutions that may be made are (i) between serine (S) and threonine (T); (ii) between proline (P) and glycine (G); and (iii) among alanine (A), valine (V), leucine (L) and isoleucine (I). Those skilled in the art may easily construct the DNAs encoding for the conservative amino acid variants through DNA recombination and synthesis techniques.

A variant of a polynucleotide or polypeptide may be naturally occurring such as an allelic variant, or it may be a variant that is not known to occur naturally. Non-naturally occurring variants of polynucleotides and polypeptides may be made by mutagenesis techniques or by direct synthesis. In addition, the variants include polypeptides modified by at least one post-translation such as glycosylation, phosphorylation, methylation, or ADP ribosylation. The variants of the polynucleotide include polynucleotides including splice variants, allelic variants, and single nucleotide polymorphisms (SNPs).

The terms "sequence homology" reflect the relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared. Homology refers to the percentage of identical residues between two sequences. For example, for two peptide sequences, homology refers to a percentage of identical amino acids between the two sequences. Methods for comparing the identity and homology of two or more sequences are well known in the art. Thus, for instance, programs available in the Wisconsin Sequence Analysis Package, version 9.1 (Devereux J et al., Nucleic Acids Res, 12, 387-395, 1984, available from Genetics Computer Group, Inc., Madison, Wis., USA), for example, the programs BESTFIT and GAP, may be used to determine the % identity between two polynucleotides and the % identity and the % homology between two polypeptide sequences.

BESTFIT uses the "local homology" algorithm of Smith and Waterman (J. Mol. Biol, 147, 195-197, 1981) and finds the best single region of similarity between two sequences. BESTFIT is further suitable for comparing two polynucleotides or two polypeptide sequences, which have different lengths, and estimates that a shorter sequence represents a longer part.

GAP arranges two sequences and finds "the maximum similarity" between them according to the algorithm of Needleman and Wunsch (J Mol Biol, 48, 443-453, 1970). GAP is further suitable for comparing sequences having approximately the same lengths, and it is expected that the arrangement occurs throughout the total length. It is preferable that gap weights and length weights used in the respective programs are 50 and 3 for a polynucleotide sequence, and 12 and 4 for a polypeptide sequence.

Other programs for determining identity and/or similarity between sequences are also known in the art, for instance the BLAST family of programs (Altschul S F et al., J Mol Biol, 215, 403-410, 1990, and Altschul S F et al., Nucleic Acids Res., 25:389-3402, 1997, available from National Center for Biotechnology Information (NCBI) in Bethesda, Md., USA) and FASTA (Pearson W R and Lipman D J. Proc Nat Acad Sci USA, 85, 2444-2448, 19988, available, e.g., as a part of the Wisconsin Sequence analysis package).

The term "biomass" refers to a certain substance containing an organic component which can be used in a production system for producing an energy source such as ethanol, carbohydrates, gasoline, natural gas, methane, biodiesel and hydrogen gas or for producing electricity, plastics, polymers, nutrients (for a human or an animal), proteins, biomolecules, drugs (for a human or an animal), fertilizers or other products, or a combination thereof.

The term "lignocellulosic biomass" refers to organic substances (wood or non-wood) derived from predetermined plants which are available for energy production on the basis of environment-friendly standards. For example, the lignocellulosic biomass may include agricultural wastes and residues such as corn stover, wheat straw, rice straw, and sugar cane bagasse. The lignocellulosic biomass may also include wood, wood energy crops, wood wastes and residues, for example, thinned coniferous trees (softwood), tree bark waste, sawdust, paper/pulp industrial waste vapor, wood fiber, grasses such as switchgrass, garden wastes (e.g., cut grass, fallen leaves, cut wood, and bush), and vegetable wastes. A lignocellulosic biomass may be a certain type of plant biomass, for example, bean stover, corn stover, rice straw, chaff, barley straw, cornstalk, wheat straw, canola straw, oat straw, oat skin, corn fiber, recycled wood pulp fiber, sawdust, hardwood, coniferous trees, or a combination thereof. Cellulose wastes, newspapers, or and cardboard may also be a lignocellulosic biomass.

The term "pretreatment of a biomass" refers to a process of changing the chemical or physical structure of components in the biomass to make the biomass easily degraded into monosaccharides in a subsequent hydrolysis step. For example, the pretreatment of a biomass may involve changing the chemical bonding or conformation of a three-dimensional structure of the components, thereby removing a non-sugar part, and making a loose tissue to facilitate enzymatic saccharification to be performed later. The pretreatment of the biomass may also involve a change in molecular structure, oxidation of the components in the biomass, changes in average molecular weight, average degree of crystallization, surface area, degree of polymerization, degree of porosity, and degree of branching, grafting, and changes in size of a crystallized region and size of the entire region.

The term "biofuel" refers to a fuel produced partially or entirely from biomass.

Isolated Polypeptide

Some proteins which do not themselves have polysaccharide hydrolytic activity are known to enhance the activity of a polysaccharide hydrolase when used in conjunction with the hydrolase, for example, cellulose-binding domain (CBD) protein, glycoside hydrolase family 61 (GH61) proteins and expansin.

Expansin proteins are known to be involved with growth control of plant cell walls, and to bind to a polysaccharide of the cell wall, thereby breaking hydrogen bonds in the polysaccharide. Expansin proteins are typically about 250-275 amino acids long and are made up of two domains preceded by a signal peptide, which is removed from the mature protein. The amino-terminal expansin domain 1 is structurally related to glycoside hydrolase 45 (GH45) family proteins and the carboxy-terminal domain is similar to a group of secreted proteins called group 2/3 grass pollen allergens (Grp2/3). A number of proteins in bacteria and fungi are known to have sequence similarity to plant expansins. No enzymatic activity has been detected in expansins.

The isolated polypeptide disclosed herein destroys hydrogen bonds in a polysaccharide or degrades the mechanical properties of the polysaccharide, thereby greatly increasing activity of a polysaccharide hydrolase in hydrolyzing polysaccharide treated with the isolated polypeptide. The isolated polypeptide is capable of binding to the polysaccharide.

The isolated polypeptide disclosed herein includes either a GH45 domain or a pollen-allergen domain (Grp2/3), but not both.

In an exemplary embodiment, an isolated polypeptide is disclosed which (a) increases activity of a polysaccharide hydrolase, (b) is capable of binding to a polysaccharide, (c) is deficient of the polysaccharide hydrolase activity, and (d) includes either a glycoside hydrolase 45 (GH45) domain or a pollen-allergen domain. Here, the term "deficient of the polysaccharide hydrolase activity" means that hydrolysates of polysaccharide such as glucose, cellooligosaccharides are not detected after enzymatic reaction with the isolated polypeptide and cellulose. For example, after enzymatic reaction with the isolated polypeptide and cellulose, either glucose or cellooligosaccharides hydrolyzed from cellulose are not detected from determination of reducing sugar by 3,5-dinitrosalicylic acid (DNS) or from HPLC analysis.

Examples of the polysaccharide hydrolase include cellulase, hemicellulase, α-amylase, glucoamylase, pectinase, xylanase, cellobiase, and a combination thereof. These polysaccharide hydrolases can produce monosaccharides by hydrolyzing cellulose, hemicellulose, glucose, xylose, pectin, xylan, or a combination thereof.

The GH45 domain or the pollen-allergen (Grp2/3) domain may be derived from an expansin protein, an expansin-like protein or a bacterial protein. Here, the term "expansin-like protein (EXLX1)" refers to a protein having similarity with expansin superfamily in structure.

The sequences of the GH45 domain and the pollen-allergen domain of various expansin or expansin-like proteins such as EXPA (α-expansin), EXPB (β-expansin), EXLA (expansin-like A), EXLB (expansin-like B), EXLX (expansin-like group X), *Arabidopsis thaliana* (At) EXPA, *Arabidopsis thaliana* (At) EXPB, *Bacillus subtilis* (Bs) EXLX, *Hahella chejuensis*(Hc) EXLX2, and *Stigmatella urantiaca* (Sa) EXLX are aligned. Examples of fungal or bacterial proteins including a GH45 domain or a pollen-allergen domain are the following (the numbers in brackets represent GenBank "GenInfo Identifier" sequence identification numbers for the protein sequence of the organism having the GH45 or Grp2/3 domain):

1. *Leptothrix cholodnii*, Lch (gi|171061047);
2. *Clavibacter michiganensis*, Cmi (gi|148272660);
3. *Nakamurella multipartite*, Nmu (gi|229224499);
4. *Frankia* sp., Fsp (gi|158317309);
5. *Micromonospora* sp., Msp (gi|238061663);
6. *Streptomyces sviceus*, Ssv (gi|254404534);
7. *Catenulispora acidiphila*, Cac (gi|229246366);
8. *Plesiocystis pacifica*, Ppa (gi|149922302);
9. *Herpetosiphon aurantiacus*, Hau (gi|159898342);
10. *Chloroflexus aurantiacus*, Cau (gi|163845817);
11. *Acidovorax avenae*, Aav (gi|120612050);
12. *Roseiflexus* sp., Rsp (gi|148655687);
13. *Myxococcus xanthus*, Mxa (gi|108762346);
14. *Stigmatella aurantiaca*, Sau (gi|115373847);
15. *Xanthomonas campestris*, Xca (gi|188990055);
16. *Ralstonia solanacearum*, Rso (gi|83747707);

17. *Xylella fastidiosa*, Xfa (gi|71275113);
18. *Pectobacterium atrosepticum*, Pat (gi|50121146);
19. *Dickeya zeae*, Dze (gi|251789717).

The GH45 or the Grp2/3 domain may be obtained from the parent protein by hydrolysis with an appropriate protease to yield the domain as one of the hydrolytic products from the parent protein. Further purification of the isolated domain can be performed.

Alternatively, the coding nucleotide sequence of the GH45 or the Grp2/3 domain can be obtained from the cDNA sequence of the parent protein by any method known in the art, e.g., by restriction cleavage of the parent protein cDNA to yield a polynucleotide encoding the desired GH45 or Grp2/3 domain or by synthesis of the sequence encoding the GH45 or Grp2/3 domain. The polynucleotide encoding for the GH45 or Grp2/3 domain can be inserted into an appropriate expression vector, which can then be introduced into a host cell in which the GH45 or Grp2/3 domain polypeptide can be expressed from the coding sequence.

In one exemplary embodiment, the GH45 domain may have a sequence homology of at least 70, 75, 80, 85, 90, 95, or 99% with the amino acid sequence of SEQ ID NO: 1 or the cDNA sequence of SEQ ID NO:4. The pollen-allergen (Grp2/3) domain may have a sequence homology of at least 70, 75, 80, 85, 90, 95, or 99% with an amino acid sequence of SEQ ID NO: 2 or the cDNA sequence of SEQ ID NO:5. Such a GH45 domain or pollen-allergen (Grp2/3) domain may be derived from, for example, *Bacillus subtilis* (Bs) EXLX1. The molecular function of BsEXLX1 is similar to that of plant expansin and was reported to bind to CPs such as cellulose and peptidoglycan and enhance cellulase activity, indicating that this protein can be used to convert cellulosic biomass to sugars.

As described above, the isolated polypeptide including either a GH45 domain or a pollen-allergen domain is significantly smaller than a protein including both a GH45 domain and a pollen-allergen (Grp2/3) domain, such as an expansin. The isolated polypeptide disclosed herein may have a theoretical pI of about 5 to 10. The isolated polypeptide may have a weight average molecular weight of about 5,000 to 20,000, but is not limited thereto.

The isolated polypeptide disclosed herein can stimulate the ability of a polysaccharide hydrolase to degrade a polysaccharide, e.g., to stimulate the ability of cellulase to degrade cellulose, and is capable of binding to a complex polysaccharide such as cellulose. Thus, the isolated polypeptide may be used in a saccharification process to obtain biofuel from a cellulosic or lignocellulosic biomass. The isolated polypeptide may also be used as an affinity tag by binding to the polysaccharides.

Composition Increasing Activity of Polysaccharide Hydrolase

In another embodiment, a composition including isolated polypeptide described above is provided.

The isolated polypeptide, as described above, may include either a GH45 domain or a pollen-allergen domain, and may be derived from expansin or an expansin-like protein The expansin or expansin-like protein may be derived from a bacterium, such as those disclosed above.

The isolated polypeptide is capable of binding to a polysaccharide such as cellulose, and greatly increases activity of a polysaccharide hydrolase by breaking hydrogen bonds in the polysaccharide or degrading its mechanical properties. Thus, the composition disclosed herein may be used as a composition for increasing activity of a polysaccharide hydrolase.

The polysaccharide hydrolase is selected from the group consisting of cellulase, hemicellulase, α-miylase, glucoamylase, pectinase, xylanase, cellobiase, and combinations thereof; and the polysaccharide may be, but is not limited to, cellulose, hemicellulose, glucose, xylose, pectin, xylan, and combinations thereof.

Polynucleotide

In another embodiment, a polynucleotide encoding the isolated polypeptide is disclosed herein. The polynucleotide can be used to produce isolated polypeptide by expression in an appropriate expression system.

The polynucleotide may be a recombinant polynucleotide. A recombinant polynucleotide means a synthetic polynucleotide or another polynucleotide manipulated in vitro. The recombinant polynucleotide may be used to produce a genetic product encoded by the polynucleotide in a cell or another biological system. For example, a cloned polynucleotide may be inserted into a suitable expression vector (e.g., a plasmid), and the plasmid may be used to transform a suitable host cell. The host cell including the recombinant polynucleotide may be referred to as a "transformed host cell." Further, a recombinant polypeptide may be produced by expressing the gene in the transformed host cell. The recombinant polynucleotide may include non-coding functional sites (e.g., a promoter, a transcription origin, a ribosome-binding site, etc.). Thus, when there is a functional linkage between a polynucleotide expression control sequence (e.g., a promoter or another transcription control sequence) and a desired polynucleotide sequence (e.g., a natural or recombinant polynucleotide), a polynucleotide is operably-linked to a control sequence. Here, the expression control sequence directs transcription of the polynucleotide.

The expression control sequence or promoter is an expression control sequence directing the transcription of the polynucleotide, which may be a foreign or natural polynucleotide. The promoter includes a nucleic acid sequence near a transcription initiation site such as a polymerase binding site. The promoter may include a terminal enhancer or repressor factor.

Examples of suitable vectors include bacteria, plasmids, phages, cosmids, episomes, virus, and insertable DNA fragments. A plasmid refers to a cyclic double-stranded DNA in which an additional DNA fragment can be inserted. A protein or polypeptide encoded by the polynucleotide described above may be produced by introducing the vector into a host cell. The vector may also include an additional control sequence. Examples of suitable control sequences may include a Shine-Dalgarno sequence in a replicase gene of phage MS-2 and a Shine-Dalgarno sequence in cII of bacteriophage λ. The expression vector may also include a suitable marker necessary to select a transformed host cell.

Various methods of introducing the polynucleotide or vector into the host cell are known in the art. For example, these methods include calcium phosphate transfection, DEAE-dextran-mediated transfection, transvection, microinjection, cationic lipid-mediated transfection, electroporation, transduction, scrape loading, ballistic introduction, and infection. These techniques may be used on various expression systems such as chromosome, episome, and virus-derived systems, bacterial plasmids, bacteriophages, transposons, enzymatic episomes, insertion elements, yeast chromosome elements, and viral vectors.

The expression system may control expression and include a control region. Generally, to produce a polypeptide in a host cell, any system or vector capable of maintaining, proliferating or expressing a polynucleotide may be used. An exemplary overexpression method of the inventive concept is a method using a plasmid vector.

Method of Degrading Polysaccharide

In another embodiment, a method of degrading a polysaccharide using the isolated polypeptide described above is provided.

In one embodiment, the method of degrading a polysaccharide includes providing a polysaccharide material, or a mixture or complex thereof, and adding to the polysaccharide material, or the mixture or complex thereof, an amount of the isolated polypeptide effective for stimulating the hydrolysis of a polysaccharide. The effective amount for stimulating the hydrolysis of a polysaccharide may be selected according to the type and characteristic of the polysaccharide, and may be, but is not limited to, about 1 to about 1000 nmole per gram of the polysaccharide, or about 100 to about 800 nmole per gram of the polysaccharide.

According to the method of degrading a polysaccharide, the hydrolytic capability of a hydrolase is increased by the presence of isolated polypeptide disclosed herein, and thereby the amount of the hydrolase required to degrade the polysaccharide and the degradation time may be reduced, resulting in excellent economic feasibility and process efficiency.

The polysaccharide material may be, but is not particularly limited to, cellulose, hemicellulose, glucose, xylose, pectin, or xylan as described above, or a complex or mixture thereof. In one example, the polysaccharide material may be obtained from a glucose biomass, a cellulosic or lignocellulosic biomass, or an algae biomass.

A source of the cellulosic or lignocellulosic biomass may be, but is not limited to, rice straw, hard wood, soft wood, herbs, recycled paper, waste paper, core, pulp and paper wastes, waste wood, thinned wood, cornstalk, corn cobs, chaff, wheat straw, sugarcane stalk, palm tree residual products, bagasse, agricultural residual products, agricultural wastes, livestock excretions, or a mixture thereof.

Such a cellulosic or lignocellulosic biomass may be pretreated prior to the degradation of the polysaccharide. The pretreatment may be performed using heat, an acidic or basic material, or a combination thereof.

In one embodiment, a hydrolase, a hydrolysis catalyst, an acid, a microorganism, or a combination thereof may be added. Such a polysaccharide hydrolase and so on may be added to the polysaccharide material along with the isolated polypeptide or after the addition of the isolated polypeptide.

In some embodiments, after the isolated polypeptide is added, the isolated polypeptide that does not bind to the polysaccharide material is removed by washing the polysaccharide material. After the washing, at least one of a polysaccharide hydrolase, a hydrolysis catalyst, an acid, and a microorganism is added to the polysaccharide material. The isolated polypeptide may be removed by washing with for example, water or a buffer solution, but is not limited thereto.

In the embodiment described above, after the isolated polypeptide is incubated with the polysaccharide for a predetermined time to bind to the polysaccharide, the polysaccharide may be washed for separation and removal of non-binding polypeptide, and then a polysaccharide hydrolase may be added thereto. In this embodiment, as well as in others, the isolated polypeptide described above can function properly to increase susceptibility of the polysaccharide to degradation by the polysaccharide hydrolase. When the isolated polypeptide disclosed herein is in contact with the polysaccharide, good hydrolysis capability, that is, a high yield of producing reducing sugar, may be obtained in an environment with a lower concentration of hydrolase than is needed in the absence of the isolated polypeptide.

As described above, the hydrolase may include one of the industrial hydrolases such as cellulase, hemicellulase, α-amylase, glucoamylase, pectinase, xylanase, cellobiase, or a mixture thereof. A concentration of the polysaccharide hydrolase may be about 2 to about 60 FPU per unit gram of the polysaccharide, but is not particularly limited thereto.

In some embodiments, diluted sulfuric acid or a microorganism capable of producing one of the hydrolases may be added to the polysaccharide material. The microorganism may be, for example, a bacterium, a yeast, or a mold.

A biofuel, such as an alcohol, may be produced by the fermentation of the monosaccharides obtained from hydrolysis of the polysaccharide material.

In another embodiment, biofuel may be produced by fermenting the reducing sugar yielded by degrading the polysaccharide. In some embodiments of the method of producing a biofuel from a polysaccharide material, the method comprises adding to the polysaccharide material an effective amount of the isolated polypeptide disclosed herein for stimulating hydrolysis of the polysaccharide; washing the polysaccharide material to remove unbound isolated polypeptide; incubating at least one of a polysaccharide hydrolase, a hydrolysis catalyst, an acid, and a microorganism with the polysaccharide material to obtain monosaccharides; and fermenting the monosaccharides using a fermenting microorganism to obtain a biofuel. The method can further comprise removing the biofuel from the fermentation process. In some embodiments, after fermentation, the method further comprises isolating or purifying the biofuel from the reaction.

A fermentation process, as shown in the following formulae (1) and (2), is a process to convert the monosaccharides produced by saccharification into biofuel through fermentation using microorganisms.

$$C_6H_{12}O_6 \rightarrow 2C_2H_5OH + 2CO_2 \quad (1)$$

$$3C_5H_{10}O_5 \rightarrow 5C_2H_5OH + 5CO_2 \quad (2)$$

The monosaccharides used in fermentation may include at least one selected from the group consisting of glucose, galactose, a galactose derivative, 3,6-anhydrogalactose, fucose, rhamnose, xylose, glucuronic acid, arabinose, and mannose.

The fermenting microorganism may be a species of a genus selected from the group consisting of *Saccharomyces* genus, *Pachysolen* genus, *Clavispora* genus, *Kluyveromyces* genus, *Debaryomyces* genus, *Schwanniomyces* genus, *Candida* genus, *Pichia* genus, and *Dekkera* genus. Specifically, the fermentable microorganism may be *Saccharomyces cerevisiae, P. tannophilus, Sarcina ventriculi, Kluyveromyces fragilis, Zygomomonas mobilis, Kluyveromyces marxianus* IMB3, *Brettanomyces custersii*, or a combination thereof but is not limited thereto. These microorganisms are effective in ethanol fermentation. In other embodiments, a microorganism such as *Clostridium acetobutylicum, Clostridium beijerinckii, Clostriduim aurantibutylicum* or *Clostridium tetanomorphum* may be effectively used for butanol or acetone fermentation.

In some embodiments, the biofuel may be a $C_1$ to $C_4$ alcohol or a $C_2$ to $C_4$ ketone. The alcohol may include ethanol, propanol, isopropanol, butanol, isobutanol, or a mixture thereof, and the ketone may include acetone, ethylene, propylene, fatty acid methyl ester, or a mixture thereof.

Saccharification and fermentation may be performed in separate reaction vessels through separate hydrolysis and fermentation (SHF) processes, or in one reaction vessel through a simultaneous saccharification and fermentation (SSF) process. In the SHF process, saccharification and fermentation may be performed under optimized conditions. However, inhibition of the enzymes in the enzymatic hydrolysis by end-products or intermediate products may occur, requiring more enzymes to overcome this inhibition, which is uneconomical. For example, due to end-product inhibition by the end-product, glucose, the enzymatic hydrolysis reaction may be terminated due to the increase in glucose concentration. On the other hand, in the SSF process, as soon as glucose is produced in saccharification, a fermenting microorganism, e.g., yeast, consumes the glucose in fermentation and thus glucose accumulation in the reaction vessel can be minimized. As a result, end-product inhibition in the SHF process can be avoided, and hydrolysis mediated by a hydrolase can be enhanced. Further, the SSF process can reduce production costs due to low equipment costs and low input of the enzyme, and can also reduce risk of contamination due to ethanol in the reaction vessel.

The fermentation may be performed, for example, at an initial glucose concentration of about 2 to 30% (w/v), at a temperature of 25 through 37° C., at a pH of about 5.0 through 8.0, and an agitation speed of about 100 to 250 rpm, but is not limited thereto.

Hereinafter, the inventive concept will be described with reference to various examples.

Preparation of BsEXLX1 Protein

BsEXLX1 having the amino acid sequence of SEQ ID NO: 3 was obtained by cloning, expression and purification processes. For heterologous expression of BsEXLX1 in *E. coli*, we cloned the gene in a modified pET21a vector using a ligation independent cloning method, which was designed at Berkeley Structural Genomics Center (BSGC) (Lee and Kim, 2009). In order to avoid the adverse effect of signal sequence during the overexpression of the gene, the potential signal peptide in amino terminus (1-23) was excluded from the entire gene when primers were designed. The final construct has a six-histidine tag in the carboxy terminus for affinity purification. The recombinant BsEXLX1 was expressed in *E. coli* BL21 (DE3) using Luria Broth media containing ampicillin (100 μg/ml) at 37° C. For soluble expression of proteins, we decreased the growth temperature to 16° C. after induction with a final concentration of 0.1 mM isopropyl thiogalactoside (IPTG) and allowed them to continue to grow for 16 h. After harvesting and breaking the cells in a lysis buffer (10 mM Tris Cl, pH 8.0) with sonication, the crude cell extract were subjected to histidine affinity chromatography using a HisTrap column (GE Healthcare, USA) and LP system (Bio-Rad, USA). The purity of proteins was examined by SDSPAGE and the concentration was measured using a Bradford assay kit (Bio-Rad).

Preparation of the Isolated BsEXLX1 GH45 and Isolated BsEXLX1 Grp2/3

The isolated BsEXLX1 GH45 domain having the amino acid sequence of SEQ ID NO: 1 and the isolated BsEXLX1 Grp2/3 domain having the amino acid sequence of SEQ ID NO: 2 were obtained by the same processes as those of Preparation of BsEXLX1 protein as described above.

Experimental Example 1

Effects on Hydrolysis Activity of Cellulase to Filter Paper

Samples of filter paper were incubated at 50° C. for 32 hours in 50 mM citrate buffer (pH 5.0) with 0.025 FPU of cellulase and 250 nmole per gram filter paper of BsEXLX1, isolated BsEXLX1 GH45 domain (GH45), isolated BsEXLX1 pollen-allergen domain (Grp2/3), and a mixture of isolated BsEXLX1 GH45 and isolated BsEXLX1 Grp2/3, each separately. Amount of reducing sugars released was measured by 3,5-dinitrosalicylic acid (DNS). The experiment was repeated three times under each set of conditions. The average values for the three experiments are shown in FIG. 1.

Figure 1:
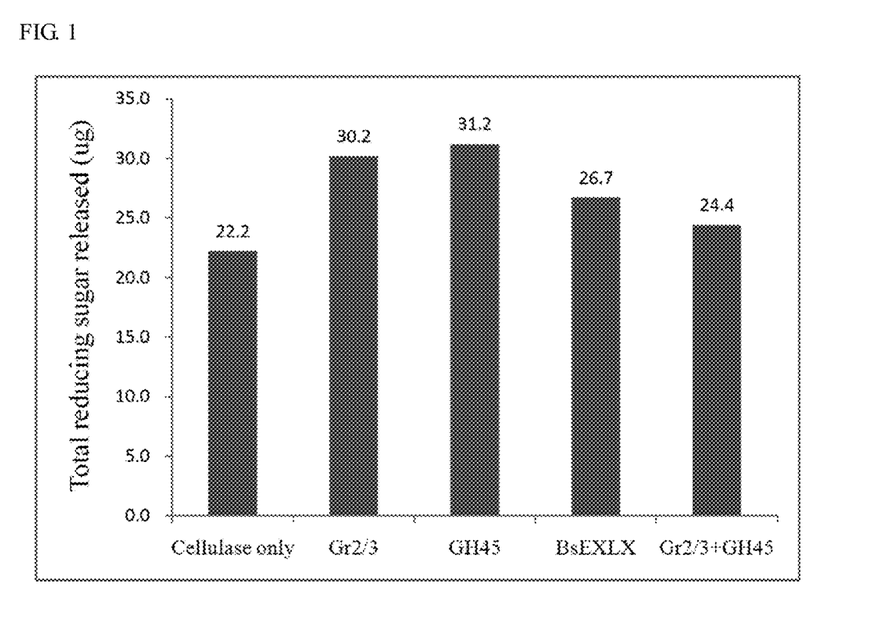
FIG. 1 is a histogram illustrating amount (μg) of total reducing sugar released in each of the cellulase reactions described in Experimental Example 1.

FIG. 1 shows that the largest amount of reducing sugar was produced when Grp2/3 or GH45 was added to the enzyme reaction. In the presence of added GH45 or Grp2/3, the amount of reducing sugar produced was about 140% of that obtained when cellulase was used alone. Addition of either BsEXLX1 or both Grp2/3 and GH45 to the cellulose reaction increased production of reducing sugar to a lesser extent.

Experimental Example 2

Effects on Hydrolysis Activity of Cellulase to Ammonia-treated Rice Straw

Rice straw was pretreated with 10% aqueous ammonia at 60° C. for 12 hours. The ammonia-treated rice straw samples were then pre-incubated in 50 mM sodium citrate buffer (pH 5.0) with or without 250 nmol of Grp2/3, GH45, BsEXLX1 at 50° C. for 32 hours.

Subsequently, the samples were washed with water to remove non-binding Grp2/3, GH45, or BsEXLX1. Then, 3 FPU of cellulase (1.5 L, Novozymes) per gram of glucan in the ammonia-treated rice straw sample was added to each sample for hydrolysis at 50° C. for 12 hours. Amount of reducing sugars released was measured by 3,5-dinitrosalicylic acid (DNS). The results are shown in FIG. 2.

Figure 2:
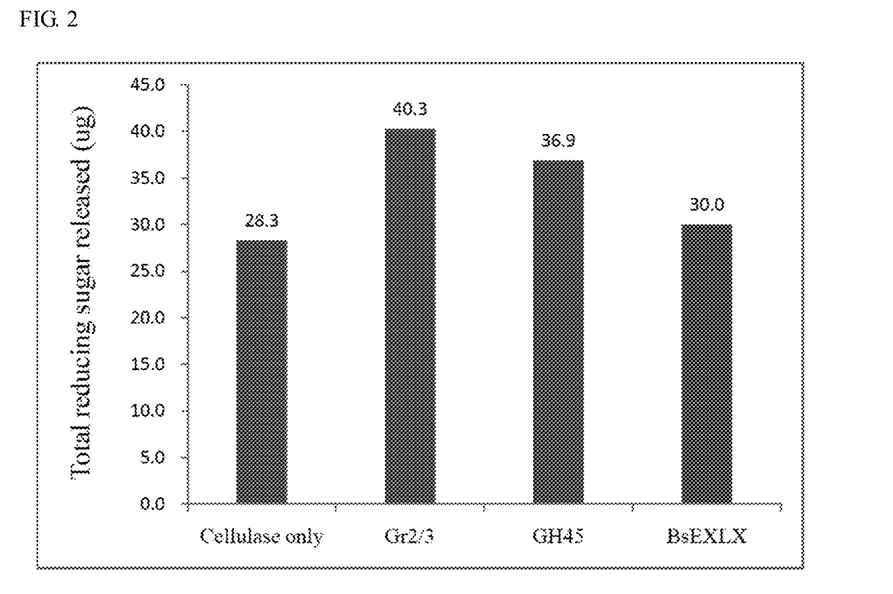
FIG. 2 is a histogram illustrating amount (μg) of total reducing sugar released in each of the cellulase reactions with rice straw described in Experimental Example 2.

FIG. 2 shows that inclusion of Grp2/3 to the cellulase reaction with the ammonia-treated rice straw, increased production of reducing sugar to at least 140% of that obtained from the cellulase reaction in the absence of Grp2/3. Similarly, addition of GH45 to the cellulase reaction increased production of reducing sugar to about 130% of that obtained from the cellulase reaction in the absence of GH45. Addition of BsEXLX1 to the cellulase reaction enhanced reducing sugar production only marginally, at best.

Comparative Example 1

Effect of BsEXLX1 on Hydrolysis Activity of Cellulase

Rice straw samples, pretreated with ammonia as described above in Experimental Example 1, were hydrolyzed in 50 mM sodium citrate buffer (pH 5.0) with or without BsEXLX1 at a concentration of 0.1, 0.3, 0.6 or 1.2 mg using 3, 6, 15, 30, or 60 FPU of cellulase (1.5 L, Novozymes) per gram of glucan at 50° C. for 72 hours. Percent total content reducing sugar was measured by 3,5-dinitrosalicylic acid (DNS). The results are shown in FIG. 3.

Figure 3:
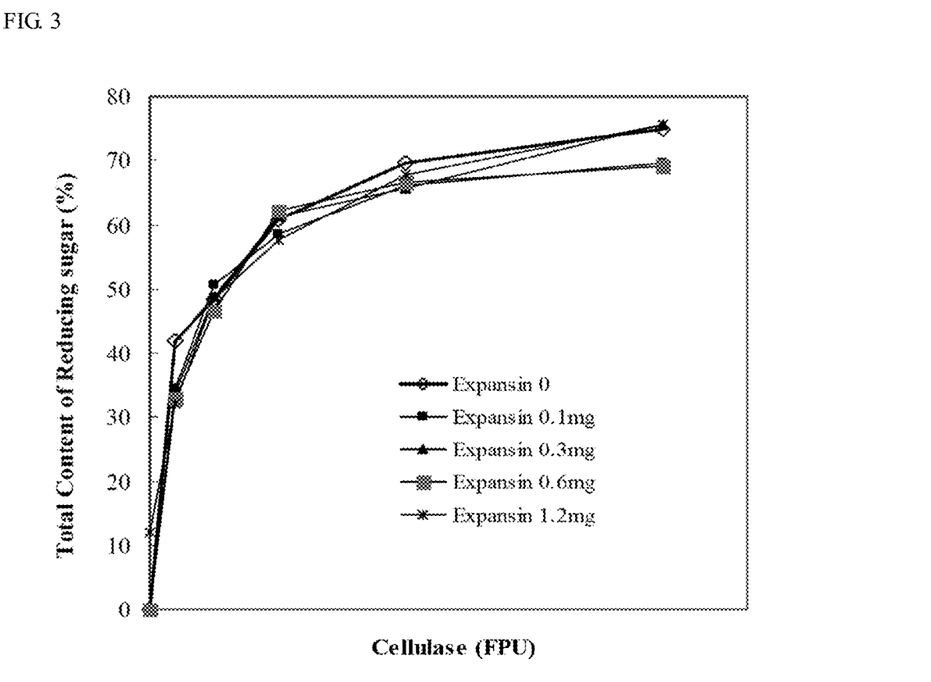
FIG. 3 is a graph illustrating cellulase amount (in FPU) vs. total content of reducing sugar (%) as a function of concentration of BsEXLX1 included in the reaction according to Comparative Example 1.

FIG. 3, shows that addition of the expansin, BsEXLX1, at any concentration between 0.1 and 1.2 mg produced no significant difference in percent yield of the reducing sugar.

Experimental Example 3

Effects in Hydrolysis Activity of Xylanae to Xylan

Insoluble xylan samples, obtained from oat spelt, were incubated in 50 mM sodium phosphate buffer (pH 7.0) with or without 625 nmol of Grp2/3, GH45, or BsEXLX1. Afterwards, the samples were hydrolyzed using 24 μg of xylanase (Xyn10C from *Saccharophagus degradans* per gram of xylan at 50° C. for 12 hours. Total reducing sugar released was measured by 3,5-dinitrosalicylic acid (DNS). The process was repeated three times. Average values are shown in FIG. 4.

Figure 4:
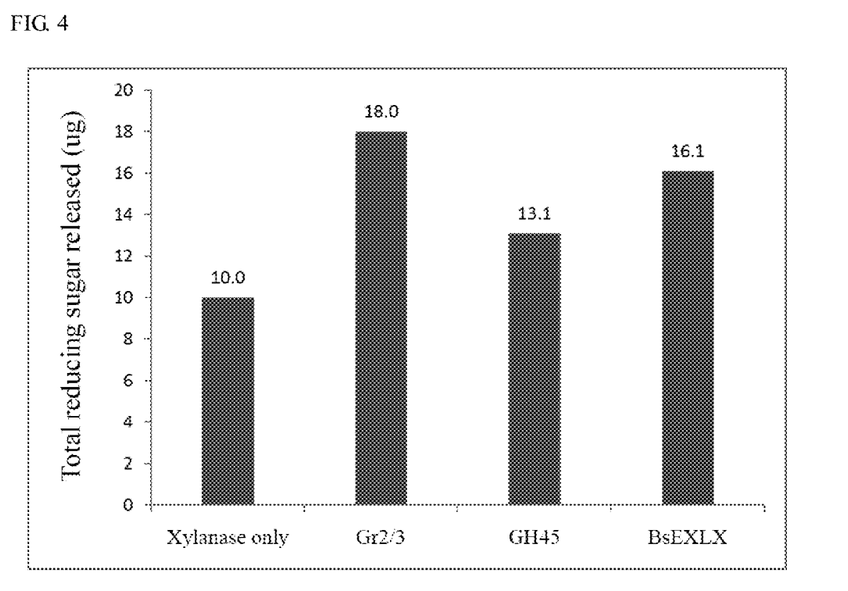
FIG. 4 is a histogram illustrating amount (μg) of total reducing sugar released in each of the xylanase reactions with xylan described in Experimental Example 3.

FIG. 4 shows that Grp2/3 showed the most significant increase in reducing sugar production, 180% increased reducing sugar released compared to when the xylanase was used alone.

While example embodiments have been disclosed herein, it should be understood that other variations may be possible. Such variations are not to be regarded as a departure from the spirit and scope of example embodiments of the present application, and all such modifications as would be obvious to those skilled in the art, are intended to be included within the scope of the following claims.

What is claimed is:

1. An isolated polypeptide consisting of SEQ ID NO:1 or SEQ ID NO:2, or a sequence that is at least 95% identical to SEQ ID NO:1 or SEQ ID NO:2, wherein the polypeptide with the sequence that is at least 95% identical to SEQ ID NO:1 or SEQ ID NO:2 (a) increases activity of a polysaccharide hydrolase, (b) binds to a polysaccharide, and (c) is deficient of polysaccharide hydrolase activity.

2. The isolated polypeptide according to claim 1, wherein the polysaccharide hydrolase is selected from the group consisting of cellulase, hemicellulase, α-amylase, glucoamylase, pectinase, xylanase, cellobiase, and a combination thereof; and the polysaccharide is selected from the group consisting of cellulose, hemicellulose, glucose, xylose, pectin, xylan, and a combination thereof.

3. The isolated polypeptide according to claim 1, wherein the isolated polypeptide is a glycoside hydrolase 45 (GH45) or pollen-allergen (Grp 2/3) domain which is separated from an expansin protein, an expansin-like protein or a bacterial protein.

4. The isolated polypeptide according to claim 3, wherein the expansin protein or the expansin-like protein is selected from the group consisting of α-expansin (EXPA), β-expansin (EXPB), expansin-like A (EXLA), expansin-like B (EXLB), expansin-like group X (EXLX), *Bacillus subtilis* (Bs)EXLX, *Hahella chejuensis* (Hc)EXLX2, and *Stigmatella aurantiaca* (Sa)EXLX.

5. The isolated polypeptide according to claim 3, wherein the bacterial protein is isolated from a bacterium selected from the group consisting of *Leptothrix cholodnii*, Lch; *Clavibacter michiganensis*, Cmi; *Nakamurella multipartite*, Nmu; *Frankia* sp., Fsp; *Micromonospora* sp., Msp; *Streptomyces sviceus*, Ssv; *Catenulispora acidiphila*, Cac; *Plesiocystis pacifica*, Ppa; *Herpetosiphon aurantiacus*, Hau; *Chloroflexus aurantiacus*, Cau; *Acidovorax avenae*, Aav; *Roseiflexus* sp., Rsp; *Myxococcus xanthus*, Mxa; *Stigmatella aurantiaca*, Sau; *Xanthomonas campestris*, Xca; *Ralstonia solanacearum*, Rso; *Xylella fastidiosa*, Xfa; *Pectobacterium atrosepticum*, Pat; and *Dickeya zeae*, Dze.

6. A composition comprising the isolated polypeptide of claim 1, wherein the isolated polypeptide comprises either a glycoside hydrolase 45 (GH45) domain or a pollen-allergen (Grp 2/3) domain derived from a bacterial expansin or an expansin-like protein.

7. The composition according to claim 6, wherein the polysaccharide hydrolase is selected from the group consisting of cellulase, hemicellulase, α-amylase, glucoamylase, pectinase, xylanase, cellobiase, and a combination thereof; and the polysaccharide is selected from the group consisting of cellulose, hemicellulose, glucose, xylose, pectin, xylan, and a combination thereof.

8. A method of degrading a polysaccharide, comprising adding an amount of the isolated polypeptide according to claim 1 effective for degrading a polysaccharide to a polysaccharide material.

9. The method according to claim 8, wherein the amount effective for degrading a polysaccharide is about 1 to about 1000 nmole per gram of the polysaccharide.

10. The method according to claim 8, wherein the polysaccharide material is obtained from a cellulosic or lignocellulosic biomass.

11. The method according to claim 10, further comprising pretreating the cellulosic or lignocellulosic biomass with heat, an acidic material, a basic material, or a combination thereof.

12. The method according to claim 8, further comprising after the isolated polypeptide is added,
washing the polysaccharide material; and
incubating the polysaccharide material with a polysaccharide hydrolase, a hydrolysis catalyst, an acid, a microorganism, or a combination thereof, such that monosaccharides are produced.

13. The method according to claim 8, wherein the isolated polypeptide is separated from an expansin protein or an expansin-like protein.

14. The method according to claim 13, wherein the polysaccharide hydrolase is cellulase, hemicellulase, α-amylase, glucoamylase, pectinase, xylanase, cellobiase, or a combination thereof; and
wherein the polysaccharide hydrolase is added at a concentration of about 2 to about 60 FPU (filter paper unit) per unit gram of the polysaccharide.

15. The method according to claim 8, further comprising:
fermenting monosaccharides obtained from the polysaccharide material with a microorganism to obtain a biofuel.

16. A method of producing a biofuel from a polysaccharide comprising
adding to a polysaccharide material an amount of the isolated polypeptide of claim 1 effective for degrading the polysaccharide;
incubating at least one of a polysaccharide hydrolase, a hydrolysis catalyst, an acid or a microorganism with the polysaccharide material to obtain monosaccharides; and
fermenting the monosaccharides into a biofuel using a fermenting microorganism.

17. The method of claim 16, wherein the isolated polypeptide is separated from an expansin protein, an expansin-like protein or a bacterial protein.

18. The method of claim 16, wherein the expansin protein or the expansin-like protein is selected from the group consisting of α-expansin (EXPA), β-expansin (EXPB), expansin-like A (EXLA), expansin-like B (EXLB), expansin-like group X (EXLX), *Bacillus subtilis* (Bs)EXLX, *Hahella chejuensis* (Hc)EXLX2, and *Stigmatella aurantiaca* (Sa) EXLX.

19. The polypeptide of claim 1, wherein the polypeptide consists of SEQ ID NO: 1.

20. The polypeptide of claim 1, wherein the polypeptide consists of SEQ ID NO: 2.

21. The method of claim 16, wherein the polypeptide consists of SEQ ID NO: 1.

22. The method of claim 16, wherein the polypeptide consists of SEQ ID NO: 2.

* * * * *

SEQUENCE LISTING

```
<160> NUMBER OF SEQ ID NOS: 5

<210> SEQ ID NO 1
<211> LENGTH: 111
<212> TYPE: PRT
<213> ORGANISM: Artificial Sequence
<220> FEATURE:
<223> OTHER INFORMATION: GH45 Domain of BsEXLX1

<400> SEQUENCE: 1

Ala Ala Tyr Asp Asp Leu His Glu Gly Tyr Ala Thr Tyr Thr Gly Ser
 1               5                  10                  15

Gly Tyr Ser Gly Gly Ala Phe Leu Leu Asp Pro Ile Pro Ser Asp Met
            20                  25                  30

Glu Ile Thr Ala Ile Asn Pro Ala Asp Leu Asn Tyr Gly Gly Val Lys
        35                  40                  45

Ala Ala Leu Ala Gly Ser Tyr Leu Glu Val Glu Gly Pro Lys Gly Lys
    50                  55                  60

Thr Thr Val Tyr Val Thr Asp Leu Tyr Pro Glu Gly Ala Arg Gly Ala
65                  70                  75                  80

Leu Asp Leu Ser Pro Asn Ala Phe Arg Lys Ile Gly Asn Met Lys Asp
                85                  90                  95

Gly Lys Ile Asn Ile Lys Trp Arg Val Val Lys Ala Pro Ile Thr
            100                 105                 110

<210> SEQ ID NO 2
<211> LENGTH: 97
<212> TYPE: PRT
<213> ORGANISM: Artificial Sequence
<220> FEATURE:
<223> OTHER INFORMATION: Grp2/3 Domain of BsEXLX1

<400> SEQUENCE: 2

Gly Asn Phe Thr Tyr Arg Ile Lys Glu Gly Ser Ser Arg Trp Trp Ala
 1               5                  10                  15

Ala Ile Gln Val Arg Asn His Lys Tyr Pro Val Met Lys Met Glu Tyr
            20                  25                  30

Glu Lys Asp Gly Lys Trp Ile Asn Met Glu Lys Met Asp Tyr Asn His
        35                  40                  45

Phe Val Ser Thr Asn Leu Gly Thr Gly Ser Leu Lys Val Arg Met Thr
    50                  55                  60

Asp Ile Arg Gly Lys Val Val Lys Asp Thr Ile Pro Lys Leu Pro Glu
65                  70                  75                  80

Ser Gly Thr Ser Lys Ala Tyr Thr Val Pro Gly His Val Gln Phe Pro
                85                  90                  95

Glu

<210> SEQ ID NO 3
<211> LENGTH: 232
<212> TYPE: PRT
```

<213> ORGANISM: Artificial Sequence
<220> FEATURE:
<223> OTHER INFORMATION: BsEXLX1

<400> SEQUENCE: 3

```
Met Lys Lys Ile Met Ser Ala Phe Val Gly Met Val Leu Leu Thr Ile
  1               5                  10                  15

Phe Cys Phe Ser Pro Gln Ala Ser Ala Ala Tyr Asp Asp Leu His Glu
             20                  25                  30

Gly Tyr Ala Thr Tyr Thr Gly Ser Gly Tyr Ser Gly Gly Ala Phe Leu
         35                  40                  45

Leu Asp Pro Ile Pro Ser Asp Met Glu Ile Thr Ala Ile Asn Pro Ala
     50                  55                  60

Asp Leu Asn Tyr Gly Gly Val Lys Ala Ala Leu Ala Gly Ser Tyr Leu
 65                  70                  75                  80

Glu Val Glu Gly Pro Lys Gly Lys Thr Thr Val Tyr Val Thr Asp Leu
                 85                  90                  95

Tyr Pro Glu Gly Ala Arg Gly Ala Leu Asp Leu Ser Pro Asn Ala Phe
            100                 105                 110

Arg Lys Ile Gly Asn Met Lys Asp Gly Lys Ile Asn Ile Lys Trp Arg
        115                 120                 125

Val Val Lys Ala Pro Ile Thr Gly Asn Phe Thr Tyr Arg Ile Lys Glu
130                 135                 140

Gly Ser Ser Arg Trp Trp Ala Ala Ile Gln Val Arg Asn His Lys Tyr
145                 150                 155                 160

Pro Val Met Lys Met Glu Tyr Glu Lys Asp Gly Lys Trp Ile Asn Met
                165                 170                 175

Glu Lys Met Asp Tyr Asn His Phe Val Ser Thr Asn Leu Gly Thr Gly
            180                 185                 190

Ser Leu Lys Val Arg Met Thr Asp Ile Arg Gly Lys Val Val Lys Asp
        195                 200                 205

Thr Ile Pro Lys Leu Pro Glu Ser Gly Thr Ser Lys Ala Tyr Thr Val
    210                 215                 220

Pro Gly His Val Gln Phe Pro Glu
225                 230
```

<210> SEQ ID NO 4
<211> LENGTH: 333
<212> TYPE: DNA
<213> ORGANISM: Artificial Sequence
<220> FEATURE:
<223> OTHER INFORMATION: GH45 domain nucleotide (cDNA) (N-term)

<400> SEQUENCE: 4

```
gcagcatatg acgacctgca tgaaggttat gcaacgtata cagggtcagg ctattcagga    60
ggagctttcc tgctggatcc cattccttcc gatatggaga ttactgcaat aaatccggcg   120
gatctcaatt acggaggagt aaaagcggca cttgccggct cttatttgga agttgaaggg   180
ccaaaaggga aaacaaccgt atatgttact gatctttatc ccgaaggcgc tcggggagct   240
cttgatctgt cacctaatgc cttccgtaaa atcggcaata tgaaagacgg aaaaatcaat   300
attaaatggc gtgttgtcaa agccccaatc acc                                333
```

<210> SEQ ID NO 5
<211> LENGTH: 291
<212> TYPE: DNA
<213> ORGANISM: Artificial Sequence
<220> FEATURE:
<223> OTHER INFORMATION: Grp 2/3 domain nucleotide (cDNA) sequence

```
<400> SEQUENCE: 5
ggcaatttca cgtaccggat caaagaaggc agcagcaggt ggtgggcagc aatccaagtc        60
agaaatcaca agtatcctgt tatgaaaatg gaatatgaaa aggatggtaa gtggatcaac       120
atggagaaaa tggactataa ccattttgtg agtacgaatt taggtactgg ctctctcaaa       180
gtcagaatga ctgacatccg cggaaaagtt gtgaaagaca ccattccaaa gctgcctgaa       240
agcggaacgt ccaaagccta tacagtaccg ggccatgttc agtttcctga a                291
```